United States Patent
Huang et al.

(10) Patent No.: US 8,829,912 B2
(45) Date of Patent: Sep. 9, 2014

(54) TRIBOCHARGE TEST FIXTURE

(75) Inventors: Xin Huang, Shanghai (CN); Jun Hu, Kunshan (CN); Qiang Wang, Shanghai (CN)

(73) Assignee: Sabic Innovative Plastics IP B.V. (NL)

( * ) Notice: Subject to any disclaimer, the term of this patent is extended or adjusted under 35 U.S.C. 154(b) by 619 days.

(21) Appl. No.: 13/059,869

(22) PCT Filed: Aug. 26, 2009

(86) PCT No.: PCT/IB2009/053742
§ 371 (c)(1),
(2), (4) Date: Feb. 18, 2011

(87) PCT Pub. No.: WO2010/023632
PCT Pub. Date: Mar. 4, 2010

(65) Prior Publication Data
US 2011/0148427 A1 Jun. 23, 2011

Related U.S. Application Data

(60) Provisional application No. 61/092,190, filed on Aug. 27, 2008.

(51) Int. Cl.
*G01R 29/12* (2006.01)
*G01N 33/44* (2006.01)
*G01N 27/60* (2006.01)

(52) U.S. Cl.
CPC ................... *G01N 27/60* (2013.01); *G01N 33/442* (2013.01)
USPC ............................ 324/457; 324/452; 324/454

(58) Field of Classification Search
USPC .......................... 324/452, 454, 457
See application file for complete search history.

(56) References Cited

U.S. PATENT DOCUMENTS 3,775,679 A   11/1973  Abbe
4,785,237 A   11/1988  Cox
4,885,543 A * 12/1989  Smith ........................... 324/452
(Continued)

FOREIGN PATENT DOCUMENTS

FR   2878034 A1   5/2006
GB   2221310 A    1/1990
JP   62267658     11/1987

OTHER PUBLICATIONS

Sparkmuseum: Eletric Machines: (Electrostatic Electricity Generators), 2002. www.sparkmuseum.com/FRICTION.HTM.*
(Continued)

*Primary Examiner* — Jermele M Hollington
*Assistant Examiner* — Sean Curtis
(74) *Attorney, Agent, or Firm* — Cantor Colburn LLP

(57) ABSTRACT

A fixture can include a test fixture that holds an object whose electrostatic charge characteristics are to be measured, means for moving a piece of rubbing material into contact with the object, and means for rubbing a surface of the object. A method for measuring the electrostatic charge characteristics of an object using a test fixture can include: placing the object in the test fixture, moving a piece of rubbing material into contact with the object and rubbing a surface of the object with the piece of rubbing material for a period of time. The rubbing causes an electrostatic charge to be built up on the surface of the object. The electrostatic charge characteristics of the object can be measured and the measured electrostatic charge characteristics of the object can be displayed.

20 Claims, 7 Drawing Sheets

(56) References Cited

U.S. PATENT DOCUMENTS

| | | | |
|---|---|---|---|
| 4,922,182 | A | 5/1990 | Cox |
| 4,983,923 | A * | 1/1991 | Taniguchi ............... 324/454 |
| 5,233,291 | A | 8/1993 | Kouno et al. |
| 5,475,319 | A | 12/1995 | Hirae et al. |
| 5,886,528 | A | 3/1999 | Perry |
| 5,888,652 | A | 3/1999 | Berbner et al. |
| 6,144,208 | A * | 11/2000 | Hearn et al. ............... 324/454 |
| 6,741,445 | B1 | 5/2004 | Phan et al. |
| 7,347,102 | B2 | 3/2008 | Moon et al. |
| 2008/0018338 | A1 | 1/2008 | Eun et al. |
| 2008/0018339 | A1 | 1/2008 | Eun et al. |

OTHER PUBLICATIONS

French Patent No. 2878034 (A1); Publication Date: May 19, 2006; Abstract Only; 1 Page.

Japanese Patent No. 62267658; Publication Date: Nov. 20, 1987; Abstract Only; 1 Page.

Monroe Electronics; Introduction to Electrostatic Voltmeters; Accessed: Jun. 20, 2008; http://www.monroe-electronics.com/esd_pages/intro_to_voltmeters.htm; 2 Pages.

Monroe Electronics; ISOPROBE Electrostatic Voltmeter, Model 244A; 2002; 2 Pages.

Monroe Electronics; Voltmeters: Models 244A, 244AK, 244AL, 279, 279L; Accessed: Jun. 25, 2008; 2 Pages.

International Search Report; International Application No. PCT/IB2009/053742; International Filing Date: Aug. 26, 2009; Date of Mailing: Dec. 7, 2009; 6 Pages.

Written Opinion of the International Searching Authority; International Application No. PCT/IB2009/053742; International Filing Date: Aug. 26, 2009; Date of Mailing: Dec. 7, 2009; 5 Pages.

Polytetrafluoroethylene; Wikipedia; Accessed: Jul. 2, 2008; http://en.wikipedia.org/wiki/Polytetrafluoroethylene; 6 Pages.

Static Generation; Generation of Static Electricity; Accessed: Jun. 20, 2008; http://www.esdsystems.com/training/staticgeneration.htm; 11 Pages.

Vosteen, William E.; "A Review of Current Electrostatic Measurement Techniques and Their Limitations"; Electrical Overstress Exposition; Monroe Electronics; Apr. 24-26, 1984; 7 Pages.

* cited by examiner

TRIBOCHARGE TEST FIXTURE

TECHNICAL FIELD

This disclosure relates in general to the measurement of the electrostatic charge or voltage built up on an object, and in particular, to apparatus and a method for the accurate and repeated automated measurement of the electrostatic charge or voltage deliberately built up on objects under test wherein the measurement of the charge retained on the objects is also a characteristic of the electric decay ability of the objects.

BACKGROUND OF INVENTION

It is desirable to measure the peak amount of static electricity or "tribocharge" and its characteristic rate of decay on various types of objects or materials (e.g., a plastic packaging material for semiconductor devices). One method for measuring the tribocharge characteristics of materials is to use a non-contact probe associated with a tribocharge meter or electrostatic voltmeter. An amount of electrostatic voltage is deliberately built up on a surface of a piece of material under test by rubbing the surface of the material. The probe measures the amount of built-up charge in a non-contact manner. The rubbing is usually performed manually by a person wearing a nitril glove to generate the electrostatic charge and corresponding voltage on the surface of the test piece.

However, this process of manually rubbing the test piece has several problems associated therewith. For example, the person performing the rubbing will invariably rub the surface of the test piece at various speeds and pressures during the rub time, which could last for a minute or so. Also, the person will likely rub different test pieces at different speeds and pressures such that there is no consistency in the rubbing (and, thus, in the generation and subsequent measurement of the static electricity) from piece to piece. This is primarily because the person performing the test receives no helpful feedback regarding the speed and/or pressure at which that person is rubbing the piece. As a result, the person inherently cannot exert any degree of control over the rubbing process and, thus, inconsistent measurement results inevitably occur. Also, the manual rubbing may induce unwanted noise into the measurement process.

Such poor repeatability and inconsistency of the manual testing process may cause difficulty, for example, in a material qualification process. Also, for some types of plastics with relatively low resistance values, the rate of decay or discharge of the electrostatic buildup on the test piece is too quick for a person to move the test piece fast enough to a position adjacent the measuring probe to accurately capture all of the desired data points in time.

What is needed is a method and apparatus for the automated rubbing of a test piece of material to generate an electrostatic charge on a surface of the test piece and to measure the peak voltage associated with the generated charge along with its ensuing rate of decay or discharge, where the charge generation and subsequent measurement are achieved in a rapid and consistent manner with any one test piece and from piece to piece.

SUMMARY OF THE INVENTION

Disclosed herein are test fixtures the electrostatic charge characteristics of an object and methods for use thereof.

In one embodiment, the method for measuring the electrostatic charge characteristics of an object can comprise: placing the object in a test fixture, moving a piece of rubbing material within the test fixture into contact with the object, rubbing a surface of the object with the piece of rubbing material for a period of time, wherein the rubbing causes an electrostatic charge to be built up on the surface of the object, measuring the electrostatic charge characteristics of the object; and displaying the measured electrostatic charge characteristics of the object.

In one embodiment, an apparatus can comprise: a test fixture that holds an object whose electrostatic charge characteristics are to be measured, and the test fixture further including means for moving a piece of rubbing material into contact with the object and means for rubbing a surface of the object with the piece of rubbing material for a period of time, wherein the rubbing causes an electrostatic charge to be built up on the surface of the object.

The foregoing and other features of various disclosed embodiments will be more readily apparent from the following detailed description and drawings of the illustrative embodiments wherein like reference numbers refer to similar elements.

BRIEF DESCRIPTION OF THE DRAWINGS

The various embodiments can be understood with reference to the following drawings. The components are not necessarily to scale. Also, in the drawings, like reference numerals designate corresponding parts throughout the several views.

DETAILED DESCRIPTION OF THE INVENTION

Figure 1:
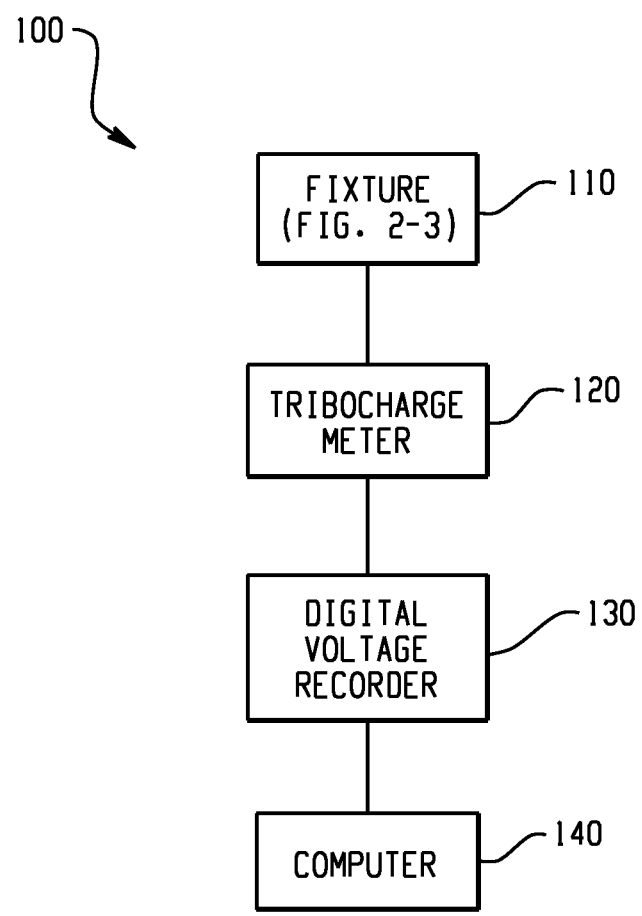
FIG. 1 is a simplified block diagram of an embodiment of an apparatus illustrating the primary components thereof.

According to an embodiment of the test fixture, the fixture includes a plate with a clamp that holds a piece of material to be tested for its electrostatic charge and discharge properties. A first cylinder connects to the fixture to raise or lower a portion of the fixture, wherein this portion of the fixture includes a first motor with an axis end that includes a spring-loaded weight holder that holds a piece of material such as, e.g., polytetrafluoroethylene (PTFE), which, when the first cylinder lowers the portion of the fixture, contacts a facing surface of the test piece for rubbing thereof to generate a tribocharge on the test piece surface. A second motor is fixed to drive a cam and connection arm, which moves the PTFE material back and forth across the surface of the test piece in addition to the rotational motion of the PTFE by the first motor. In the alternative, the first motor can be used solely to rotate the PTFE material for rubbing the test piece in a stationary position. The fixture also includes a holder for a probe that is part of a tribocharge meter. Once the surface of the test piece has been charged, a second cylinder and sliding rail portion of the fixture automatically and quickly moves the plate with the test piece over to the probe, which measures the tribocharge characteristics (e.g., peak voltage and rate of decay of the voltage) on the surface of the test piece in a non-contact manner. The charge measured by the tribocharge meter is provided to a voltage meter, which displays the resulting measured voltage in numerical form, and also provides the measured voltage to a computer. The computer displays the electrostatic voltage characteristics of the test piece in a voltage versus time graphical format on the display screen of the computer.

In one embodiment, the method for measuring the electrostatic charge characteristics of an object can comprise: placing the object in a test fixture, moving a piece of rubbing material within the test fixture into contact with the object, rubbing a surface of the object with the piece of rubbing material for a period of time, wherein the rubbing causes an electrostatic charge to be built up on the surface of the object, measuring the electrostatic charge characteristics of the object; and displaying the measured electrostatic charge characteristics of the object.

Moving a piece of rubbing material can comprise automated moving the piece of rubbing material within the text fixture into contact with the object in response to an operator command. Rubbing a surface of the object with the piece of rubbing material for a period of time can comprise rubbing the surface of the object with the piece of rubbing material in a rotational manner, a back-and-forth manner, or both a rotational manner and in a back-and-forth manner. Rubbing a surface of the object in a rotational manner, a back-and-forth manner, or both a rotational manner and a back-and-forth manner can be in response to an operator command. After rubbing a surface of the object with the piece of rubbing material for a period of time, the object can be automated moved to a test probe for measuring the electrostatic charge characteristics of the object. Measuring the electrostatic charge characteristics of the object can comprise measuring a peak voltage associated with the measured electrostatic charge and a rate of decay of the voltage associated with the measure electrostatic charge. The measured peak voltage and the measured rate of decay of the voltage can be numerically displaying, graphically displayed, or both numerically and graphically displayed. Placing the object in a test fixture can comprise securing the object in the test fixture. The various steps of the method discussed above can be used individually or in combination.

In one embodiment, an apparatus can comprise: a test fixture that holds an object whose electrostatic charge characteristics are to be measured, and the test fixture further including means for moving a piece of rubbing material into contact with the object and means for rubbing a surface of the object with the piece of rubbing material for a period of time, wherein the rubbing causes an electrostatic charge to be built up on the surface of the object.

The apparatus can comprise means for measuring the electrostatic charge characteristics of the object and/or means for displaying the measured electrostatic charge characteristics of the object. The means for rubbing a surface of the object with the piece of rubbing material for a period of time can be configured to rub (e.g., capable of rubbing) the surface of the object with the piece of rubbing material in a rotational manner, in a back-and-forth manner, or both a rotational manner and in a back-and-forth manner. The means for moving a piece of rubbing material can be configured to move (e.g., capable of moving) the piece of rubbing material into contact with the object in response to an operator command. The means for measuring the electrostatic charge characteristics of the object can comprise a tribocharge meter that can be configured to measure (e.g., capable of measuring) a peak voltage associated with the measured electrostatic charge and a rate of decay of the voltage associated with the measure electrostatic charge. The means for displaying the measured electrostatic charge characteristics of the object can comprise a voltage recorder that can be configured to numerically display (e.g., capable of numerically displaying) the measured peak voltage and the measured rate of decay of the voltage, and/or the means for displaying the measured electrostatic charge characteristics of the object can comprise a computer that can be configured to graphically display (e.g., capable of graphically displaying) the measured peak voltage and the measured rate of decay of the voltage. The various elements of the apparatus discussed above can be used individually or in combination.

The fixture and method are more particularly described in the following description and examples that are intended to be illustrative only since numerous modifications and variations therein will be apparent to those skilled in the art. As used in the specification and in the claims, the singular form "a," "an," and "the" may include plural referents unless the context clearly dictates otherwise. Also, as used in the specification and in the claims, the term "comprising" may include the embodiments "consisting of" and "consisting essentially of." Furthermore, all ranges disclosed herein are inclusive of the endpoints and are independently combinable.

As used herein, approximating language may be applied to modify any quantitative representation that may vary without resulting in a change in the basic function to which it is related. Accordingly, a value modified by a term or terms, such as "about" and "substantially," may not to be limited to the precise value specified, in some cases. In at least some instances, the approximating language may correspond to the precision of an instrument for measuring the value. Reference throughout the specification to "one embodiment", "another embodiment", "an embodiment", and so forth, means that a particular element (e.g., feature, structure, and/or characteristic) described in connection with the embodiment is included in at least one embodiment described herein, and may or may not be present in other embodiments. In addition, it is to be understood and presently contemplated that the described elements can be combined in any suitable manner in the various embodiments.

In an embodiment described in detail hereinafter, a fixture includes a plate with a clamp that holds a piece of, e.g., a flat plastic material for use, for example, as packaging material for semiconductors, to be tested for its electrostatic charge and discharge properties. However, any type of material, plastic or otherwise, and in a shape other than flat, can be tested by the test fixture. A first cylinder connects to the fixture to raise or lower a portion of the fixture, wherein this portion of the fixture includes a first motor with an axis end that includes a spring-loaded weight holder that holds a piece of material such as, e.g., PTFE, which, when the first cylinder lowers the portion of the fixture, contacts a facing surface of the test piece for rubbing thereof to generate an electrostatic voltage on the test piece surface. A second motor is fixed to drive a cam and connection arm, which moves the PTFE material back and forth across the surface of the test piece in addition to the rotational motion of the PTFE by the first motor. In the alternative, the first motor can be used solely to rotate the PTFE material for rubbing the test piece in a stationary position. The fixture also includes a holder for a probe that is part of a tribocharge meter. Once the surface of the test piece has been charged, a second cylinder and sliding rail portion of the fixture automatically and quickly moves the plate with the test piece over to the probe, which measures the tribocharge characteristics (e.g., peak voltage and rate of decay of the voltage)

on the surface of the test piece in a non-contact manner. The charge measured by the tribocharge meter is provided to a voltage meter, which displays the resulting measured voltage in numerical form, and also provides the measured voltage to a computer. The computer displays the electrostatic voltage characteristics of the test piece in a voltage versus time graphical format on the display screen of the computer.

Figure 2:
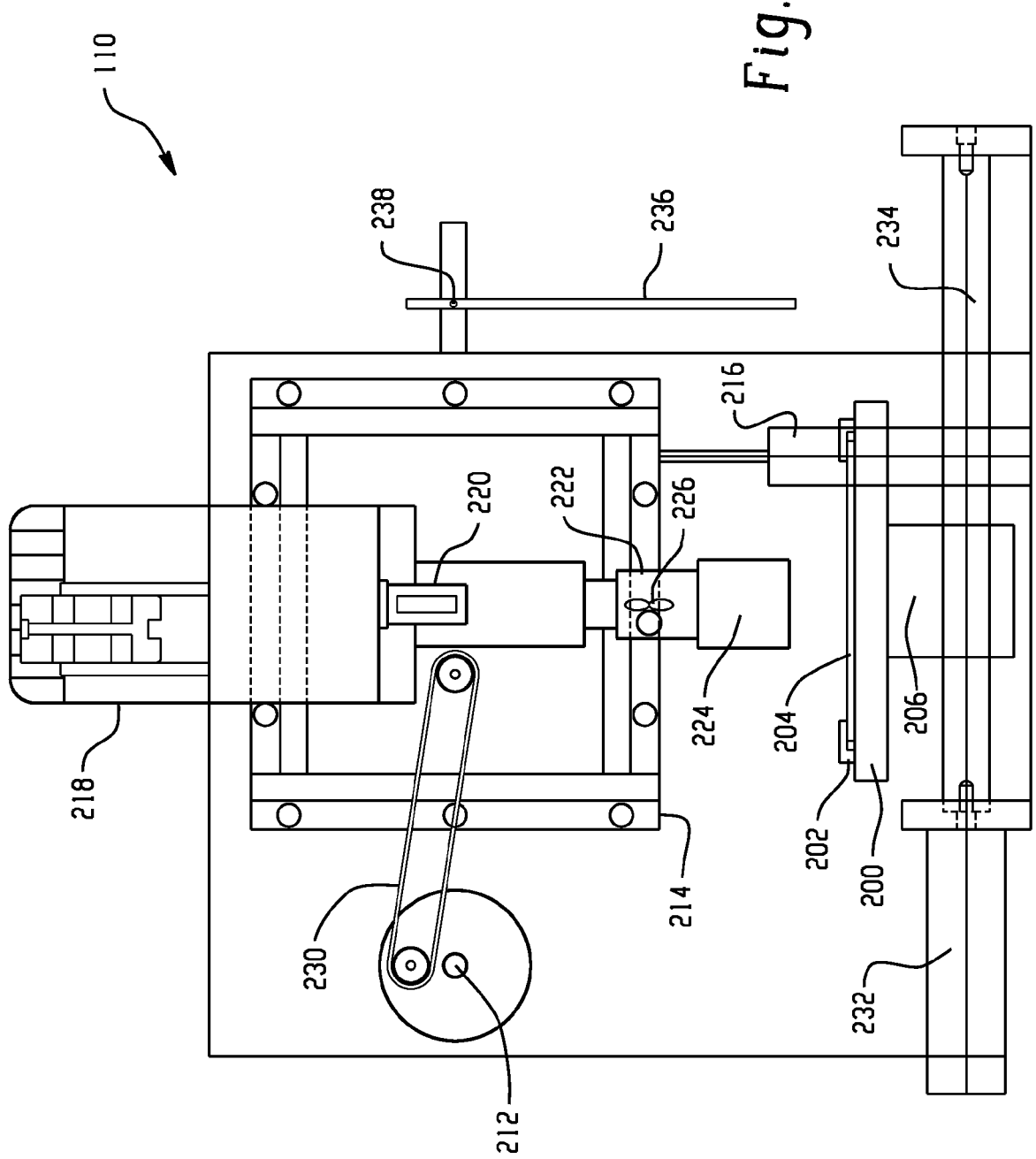
FIG. 2 is a side view of a fixture that is part of the embodiment of FIG. 1.
Figure 3:
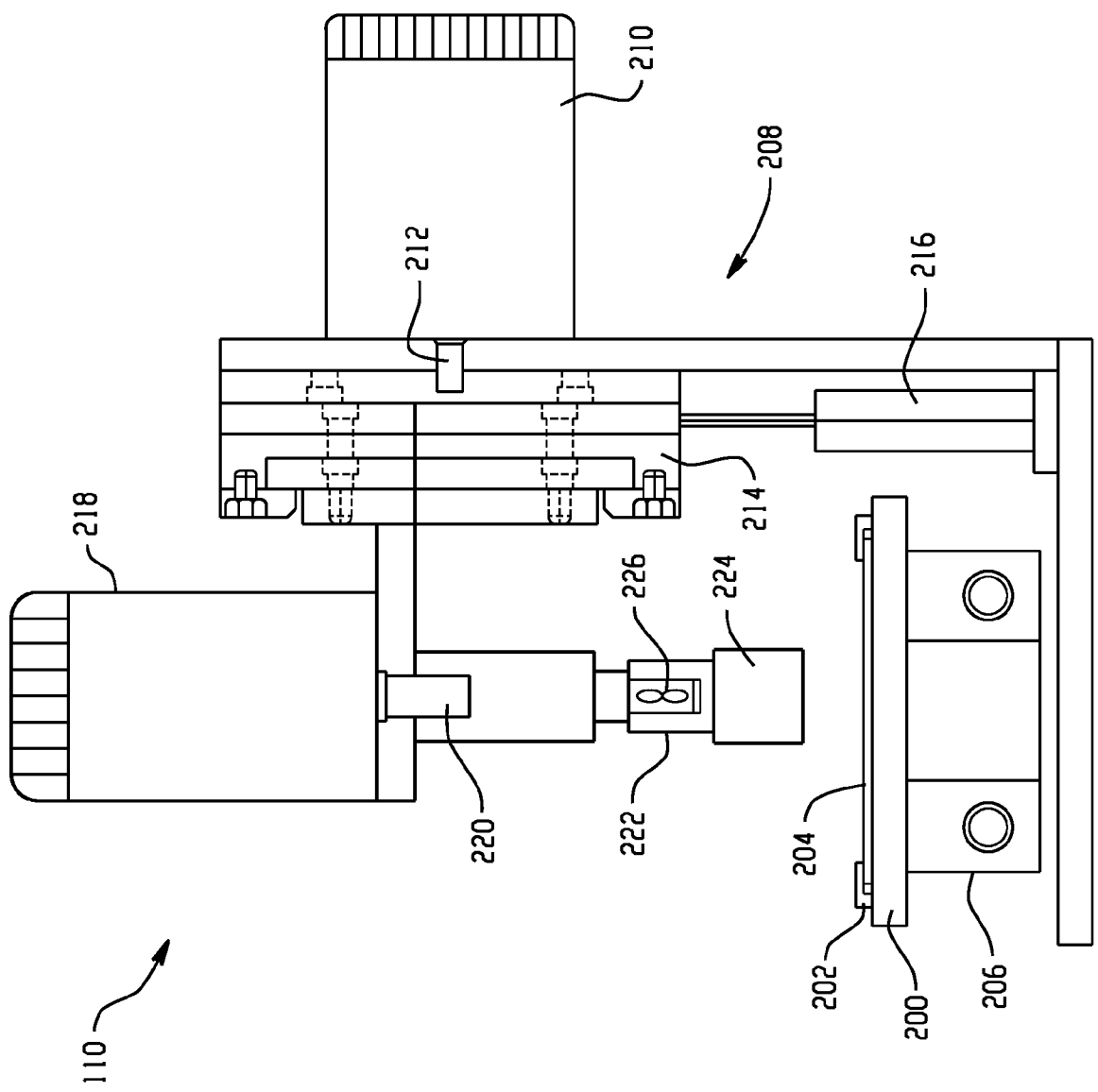
FIG. 3 is an end view of the fixture of FIG. 2.

Referring to FIG. 1, there illustrated is a simplified block diagram of an apparatus illustrating the primary components thereof. The apparatus 100 includes a fixture 110, which is illustrated in more detail in FIGS. 2-3. As described in more detail hereinafter, the fixture 110 includes components that carry out the automated rubbing of a test piece of material to generate an electrostatic charge on a surface of the test piece for subsequent measurement of the peak voltage associated with the generated charge and its ensuing rate of decay or discharge, where the charge generation and subsequent measurement are achieved in a rapid and consistent manner with any one test piece and from piece to piece. The apparatus 100 also includes a tribocharge meter or electrostatic voltmeter 120 that measures the amount of charge built up on the surface of the test piece in a non-contact manner using a probe that attaches within the fixture 110 (FIGS. 2-3). The tribocharge meter 120 can comprise the Model 244 available from Monroe Electronics, Inc. The corresponding electrostatic voltage of the measured charge is provided to a digital voltage recorder 130, which can comprise the Model DM3051 available from Rigol Technologies, Inc. The voltage recorder 130 can provide a numerical display of the measured electrostatic voltage and can also store the recorded measured electrostatic voltage data therein. The measured electrostatic voltage data can be provided by the recorder 130 to a computer 140 having a visual display for graphical display of the measured electrostatic voltage versus time characteristics of each particular test piece. The computer can use the Microsoft Excel spreadsheet application program or other spreadsheet or non-spreadsheet programs to manipulate the data for display.

Referring to FIGS. 2-3, there illustrated in more detail is the fixture 110. The fixture 110 includes a horizontally oriented plate 200 with a clamp 202 that holds a specimen or piece of material 204 for testing of its tribocharge characteristics. The test piece 204 can comprise a relatively hard piece of flat material, e.g., a plastic material for use as packaging material in the semiconductor industry. The test piece 204 can have a thickness in the range of 1 millimeter (mm)-10 mm. However, the test piece 204 can comprise any type, size and/or shape of material having electrostatic properties that are desired to be measured. In an embodiment, the size of the test piece 204 can range from 68 mm×68 mm to 160 mm×160 mm. The plate 200 can be affixed to a bottom portion 206 of the fixture 110. A vertically oriented portion 208 of the fixture 110 that is affixed to the bottom portion 206 of the fixture 110 can include a first electric motor 210 attached thereto. The shaft of cylinder 216 can attach to a vertically oriented movable plate portion 214 of the fixture. The vertically oriented plate portion 214 of the fixture 110 can move up or down while the shaft cylinder 216 moves up and down. Attached to this movable plate portion 214 of the fixture is a second electric motor 218 that has an output shaft 220 with a weight 222 attached thereto. Affixed to the weight 222 is a piece of material 224, such as PTFE, which contacts the surface of the test piece 204 when the vertically oriented plate portion 214 of the fixture 110 is moved downward by the moving of shaft of cylinder 216. The PTFE material 224 rubs the surface of the test piece 204 to generate the electrostatic charge and corresponding voltage thereon, as described in more detail hereinafter. Other materials besides PTFE can be used to rub the surface of the test piece 204 to generate the electrostatic charge thereon. A spring 226 is included on the weight 222 to insure that the bottom surface of PTFE material 224 contacts the test piece surface in an even manner throughout the rub cycle, thereby insuring that a consistent electrostatic charge is generated on the test piece surface and also that a consistent charge is generated from piece to piece. That is, the spring 226 automatically compensates for any wear of the PTFE material 224 or uneven placement of the PTFE material on the test piece surface or other factors that could cause inconsistent measurements of the electrostatic properties of a test piece 204 or from piece to piece if not for the spring.

The fixture 110 can also include a cam and connection arm arrangement 230, which causes the vertically oriented plate portion 214 of the fixture 110 to move in a back and forth manner. In turn, this type of movement results in the PTFE material 224 rubbing the test piece surface in both a back and forth manner and a rotational manner to generate the electrostatic charge thereon. In the alternative, the cam and connection arm arrangement 230 can be bypassed and the rubbing of the test piece surface can be carried out strictly in a rotational manner by the rotation of the shaft 220 of the motor 218 and the associated PTFE material 224.

The fixture 110 also includes a cylinder 232 and sliding rail 234. The cylinder 232 can comprise an electric motor or other type of mechanical actuator that attaches to the sliding rail 234. The horizontal plate 200 with the test piece 204 thereon connects with the sliding rail 234. As described in more detail hereinafter, after the rubbing motion of the PTFE material 224 on the test piece surface is complete, the cylinder 232 is actuated to move the rail 234 and thus the test piece 204 over to the left in FIG. 2, where a holder 236 for a test probe that is part of the tribocharge meter 120 is located. As a result of this movement, the probe is positioned directly over the test piece surface in a non-contacting manner (e.g., at a distance of approximately 3 mm between the tip of the probe and the test piece surface). The probe measures the electrostatic charge and corresponding voltage that has been built up on the surface of the test piece 204. The height of the test piece holder 236 above the horizontally oriented plate 200 (and thus the height of the probe tip from the test piece surface) can be adjustable through use of a screw adjustment 238.

Not shown in FIGS. 2-3 for clarity are the typical supply voltages for the motors and the actuator. These supply voltages can comprise alternating current (AC) or direct current (DC) power supplies or other common power sources. Also not shown is that the fixture 110 can be enclosed by a suitable enclosure (e.g., a metal structure with glass panels some of which can open to allow access to the fixture 110). The enclosure is utilized in an embodiment to isolate all moving parts of the fixture 110 inside the enclosure and also to eliminate any impact of stray electrostatic charge within the environment on the accuracy of the measurement of the electrostatic properties on the test piece, as stray tribocharge inherently can exist in most locations.

Figure 4:
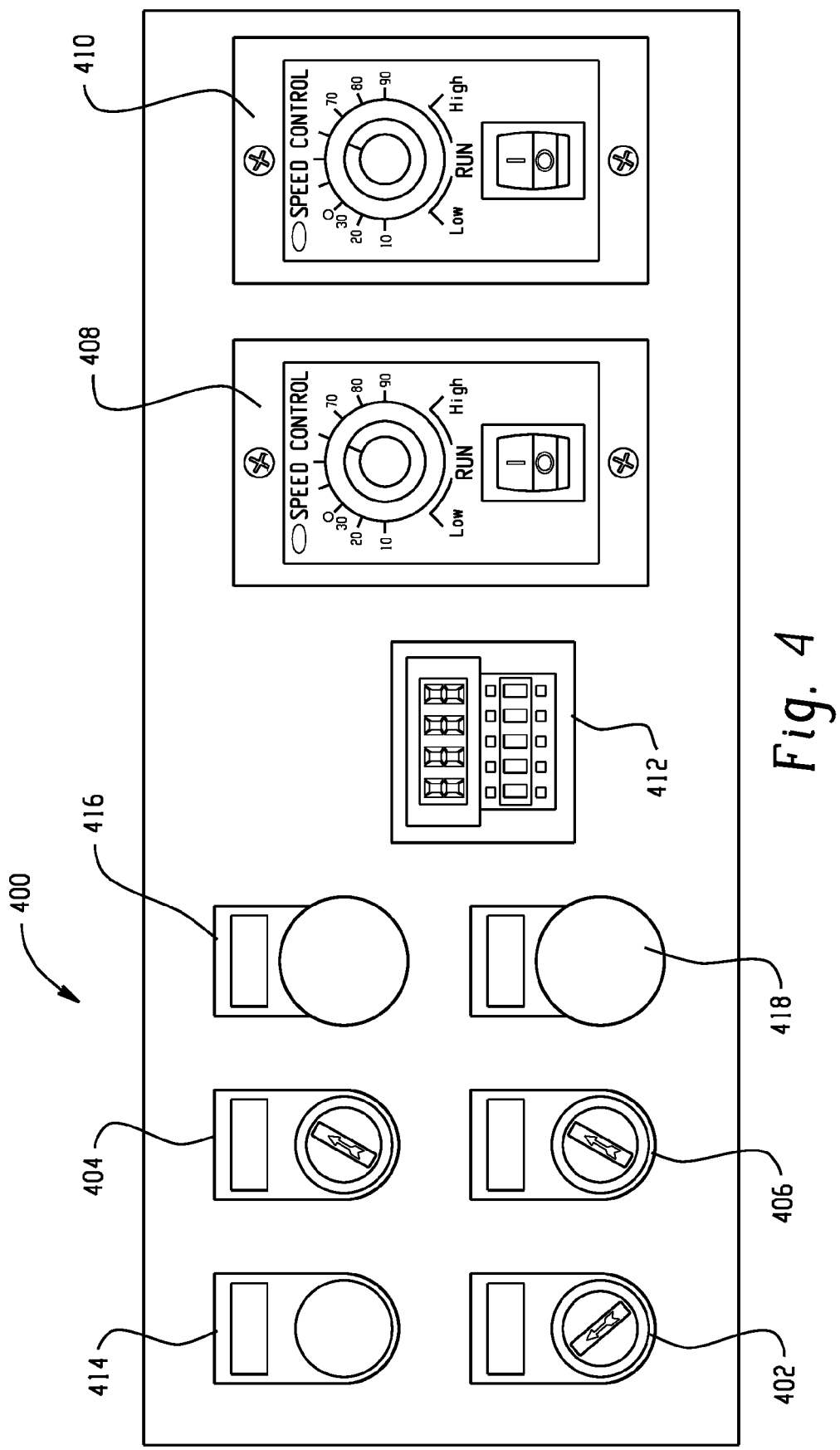
FIG. 4 is a front view of a control panel of the fixture of FIGS. 2-3.

Referring also to FIG. 4, there illustrated is an embodiment of a panel 400 (i.e., the front panel) of the fixture 110 that includes various control devices and other components for controlling the operation of an embodiment of the apparatus 100. In operation of an embodiment of the apparatus 100, a piece of material 204 or an object to be tested for its electrostatic properties is placed on and secured to the horizontally oriented plate portion 200 of the fixture 110. Electrical power is then applied to the components of the fixture 110 that require power for their proper operation by actuation of the switch 402 on the front panel 400. A rub mode is then selected, where the choices for the rub mode include solely a rotational motion of the PTFE material on the test piece surface or a back and forth rubbing motion of the PTFE material on the test piece surface together with a rotational motion of the PTFE. This choice can be made through use of the "Rub Mode I" and "Rub Mode II" switches 404, 406 on the front panel 400. A corresponding speed of the selected rubbing motion(s) can be selected through use of the "Speed Set Mode I" or "Speed Set Mode II" controls 408, 410 on the front panel 400. A timer 412 on the front panel 400 can be used to select the amount of time that the rubbing takes place. An "Instruction Light for Power" light 414 indicates when the apparatus 100 is connected to electrical power in a standby manner, ready to be started to perform the test. Conversely, when this light 414 is off, electrical power is disconnected from the apparatus 100.

Once these selections have been made, an operator activates the "Start" button 416 on the front panel and the operation of the apparatus 100 begins. An emergency stop button 418 is also provided. When operation begins, the first cylinder 216 automatically lowers the motor 218 and thus the PTFE material 224 into contact with the surface of the test piece 204 and the rubbing of the test piece surface begins. A typical amount of pressure applied by the PTFE material 224 to the test piece surface during the rubbing thereof can be approximately 1 kilograms (Kg). The rubbing can take place for approximately one minute at a rotational speed of the PTFE material in the range of from 0-90 revolutions per minute (RPMs), with an upper limit of approximately 300 RPMs. If a back and forth rubbing motion is also chosen, such back and forth motion can occur within a range of from 0-90 times per minute.

Once the rubbing motion has been completed as indicated by the timer 412 timing out, the fixture 110 automatically and quickly moves the test piece 204 over to be located underneath the probe of the tribocharge meter 120 within the probe holder 236 through use of the cylinder 232 and rail 234. The probe then measures the amount of tribocharge built up on the surface of the test piece 204 during the rubbing thereof by the PTFE material 224. The quick movement of the test piece 204 to the probe location is desired for reasons that certain types of materials (e.g., a plastic material with a relatively low amount of surface resistivity ("SR") of $10^6$ or 1 million ohms per square) has an inherently relatively quick rate of decay or discharge (e.g., 0.1 seconds) down from the peak value of the built up charge on its surface and it is desired that the tribocharge meter 120 not only measure the peak amount of built up charge but also the rate of decay of this charge on the test piece surface. It is to be noted from FIGS. 2-3 that, in an embodiment, the PTFE material 224 does not contact the entire surface of the test piece 204, even when back and forth motion of the PTFE material 224 is selected. Typically it is desired to rub the surface of the test piece 204 at the approximate center thereof.

Figure 5:
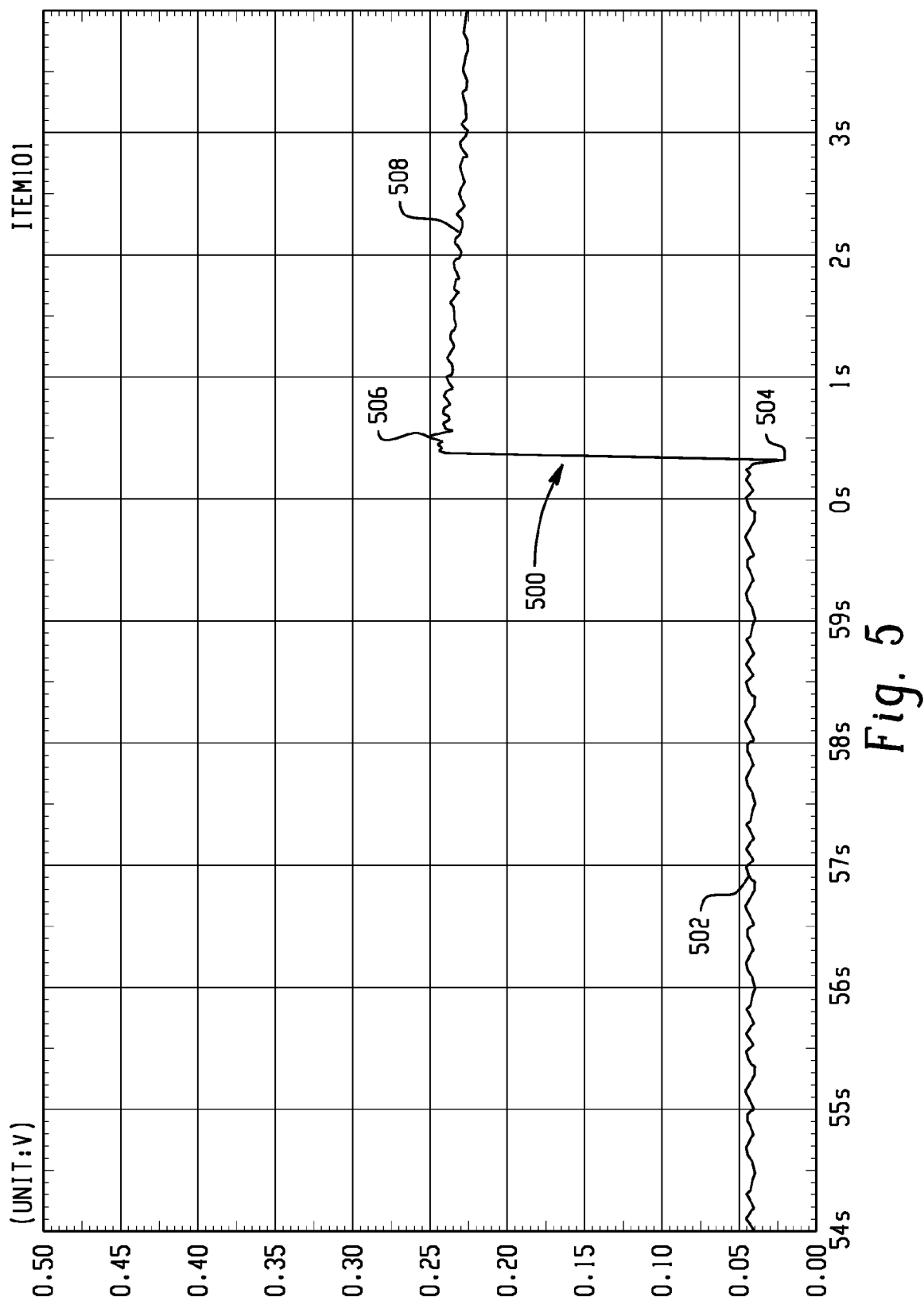
FIG. 5 is a graph of the measured electrostatic voltage versus time characteristics achieved by an embodiment of the test fixture for a test piece.

Once the rubbing of the test piece surface is complete and the test piece 204 is moved over to the location of the probe of the tribocharge meter 120, the probe measures the peak or maximum amount of electrostatic voltage generated on the test piece surface by the rubbing motion. This measured voltage is provided to the digital voltage recorder 130 where it can be numerically displayed and stored. The recorder 130 then provides the data to the computer 140. The computer 140, which can comprise any type of general-purpose personal computer (e.g., such as that provided by Dell), can contain software that takes the data and uses the Microsoft Excel spreadsheet application program or another spreadsheet or non-spreadsheet program to convert the data to a graphical display format of voltage versus time for display on a visual display monitor that is part of the computer 140. The software can be commercially available or can be a relatively simple program that merely converts the voltage data into a graphical two-dimensional display of voltage versus time. For example, FIG. 5 is a graph 500 of the measured electrostatic voltage versus time characteristic curve that was measured for a test piece that comprised a conductive carbon power filled polycarbonate material with a surface resistivity value of approximately $4.09e^{14}$ ohms per square. The first portion 502 of the graph 500 shows the amount of tribocharge in air as the test piece 204 was being rubbed for a period of time of approximately 15 seconds. During this time, the test piece 204 was not under the tribocharge meter probe and thus the probe was not measuring the voltage built up on the test piece surface. The graph 500 then illustrates the beginning 504 of the test in which the test piece 204 was moved over to be located underneath the probe and the peak voltage was measured. The graph 500 of FIG. 5 indicates that the peak voltage 506 was approximately 250 volts. The graph 500 then illustrates a relatively slow rate of decay or discharge 508 of the electrostatic voltage or charge on the test piece surface.

Figure 6:
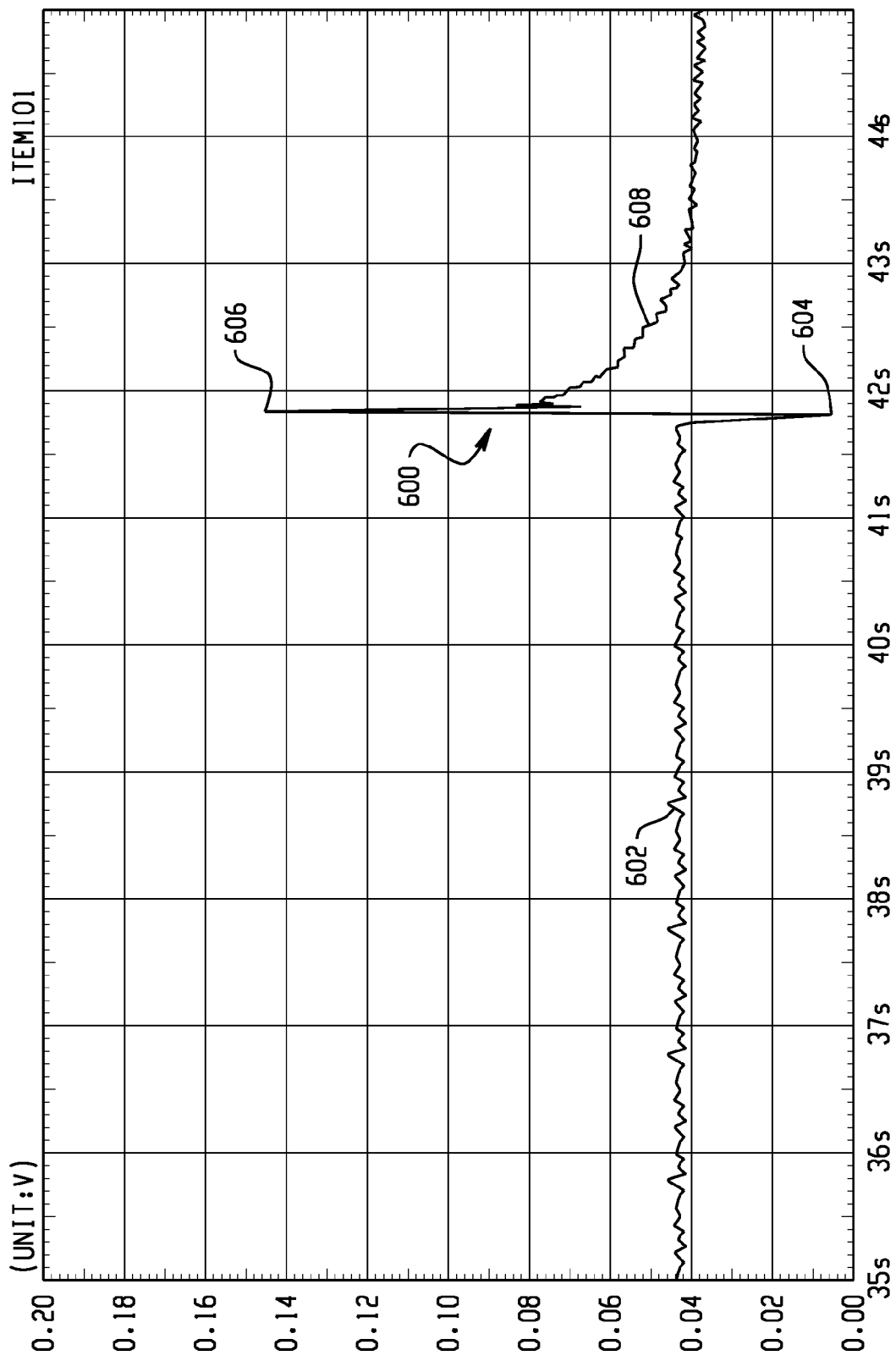
FIG. 6 is a graph of the measured electrostatic voltage versus time characteristics achieved by an embodiment of the test fixture for another test piece.

FIG. 6 illustrates another graph 600 of the measured electrostatic voltage versus time characteristic curve for a test piece 204 that comprised a conductive carbon power filled polycarbonate material with a surface resistivity of approximately $5.09e^9$ ohms per square. The first portion 602 of the graph 600 shows the amount of tribocharge in air as the test piece 204 was being rubbed for a period of time of approximately 15 seconds. The graph 600 then illustrates the beginning 604 of the test in which the test piece was moved over to be located underneath the probe and the peak voltage was measured. The graph 600 of FIG. 6 indicates that the peak voltage 606 was approximately 150 volts. The graph 600 then illustrates a relatively fast rate of decay or discharge 608 of the electrostatic voltage or charge on the test piece surface (e.g., the voltage dropped down to below 40 volts in approximately 3 seconds).

Figure 7:
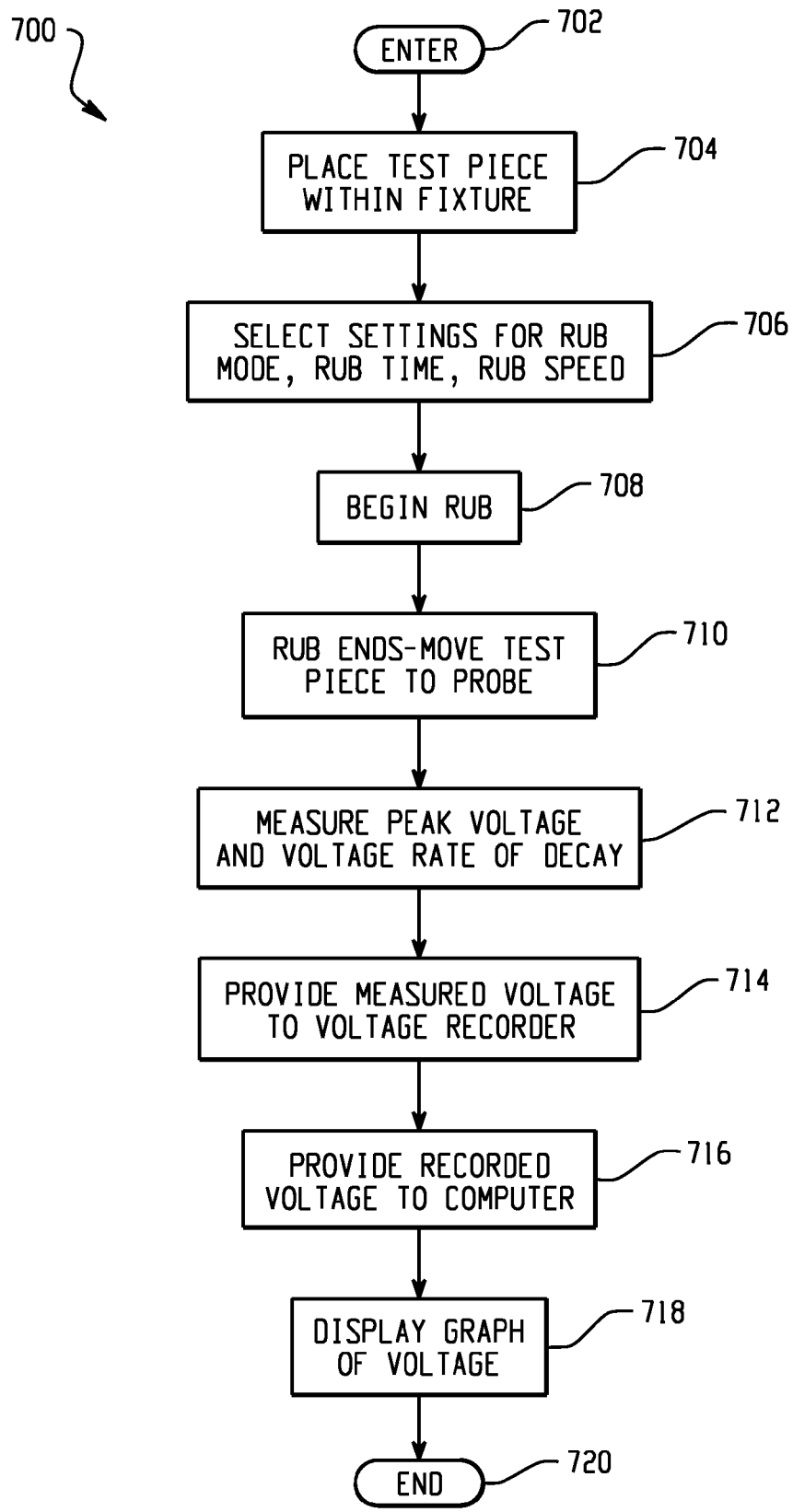
FIG. 7 is a flowchart of steps of an embodiment of a method for using the test fixture.

Referring to FIG. 7, there illustrated is a flowchart that contains the steps carried out in an embodiment of a method for using the test fixture. The method 700 enters at a step 702 after which is a step 704 in which the test piece 204 is placed within the fixture 110. A step 706 is executed in which the operator selects the settings for the rub mode, rub time and rub speed using the appropriate devices on the front panel 400 of the fixture 110. The rubbing of the test piece 204 is then started in a step 708. The rubbing continues for the set amount of time after which the rub ends in a step 710 and the test piece 204 is automatically moved over to be located underneath the non-contact probe of the tribocharge meter 120. Next, the tribocharge meter 120 measures the amount of peak electrostatic voltage and the rate of decay of this voltage in a step 712. The measured voltage is then fed to the digital voltage recorder 130 in a step 714, where the recorder 130 numerically displays the voltage and records the voltage. Next, in a step 716, the voltage recorder 130 provides the voltage data to the computer 140, which can convert the data into the Microsoft Excel spreadsheet application program format or another spreadsheet or non-spreadsheet program format. The computer 140 then runs a software program that converts the voltage data to a graphical display of voltage versus time for display on the computer visual display monitor in a step 718. The method 700 then ends in a step 720.

The embodiments of the apparatus and method overcome the problems of the manual operator testing methods described hereinabove by providing for an automated testing of the electrostatic characteristics of various types of materials. The generation of the electrostatic voltage on a surface of a test piece and the subsequent measurement of the generated voltage is carried out in an automated manner, which provides for consistency of the pressure and speed of the rubbing of the test piece surface and a resulting consistency in the voltage generation for each test piece and from piece to piece. It further provides for quick movement of the test piece to the measurement probe such that all relevant voltage data points are captured and displayed for easy viewing by an operator.

A method for measuring the electrostatic charge characteristics of an object can comprise: placing the object in a test fixture, moving a piece of rubbing material within the test fixture into contact with the object, rubbing a surface of the object with the piece of rubbing material for a period of time, wherein the rubbing causes an electrostatic charge to be built up on the surface of the object, measuring the electrostatic charge characteristics of the object, and displaying the measured electrostatic charge characteristics of the object. Optionally: (i) moving the piece of rubbing material can further comprise automated moving the piece of rubbing material within the text fixture into contact with the object in response to an operator command; (ii) rubbing the surface of the object with the piece of rubbing material for a period of time can further comprise rubbing the surface of the object with the piece of rubbing material in a rotational manner and/or in both a rotational manner and in a back-and-forth manner; (iii) after rubbing the surface of the object with the piece of rubbing material for a period of time, further comprising automated moving the object to a test probe for measuring the electrostatic charge characteristics of the object; (iv) measuring the electrostatic charge characteristics of the object can further comprise measuring a peak voltage associated with the measured electrostatic charge and a rate of decay of the voltage associated with the measure electrostatic charge, and, optionally, numerically displaying the measured peak voltage and the measured rate of decay of the voltage; (v) displaying the measured electrostatic charge characteristics of the object can further comprise graphically displaying the peak voltage associated with the measured electrostatic charge and a rate of decay of the voltage associated with the measure electrostatic charge; (vi) placing the object in a test fixture can further comprise securing the object in the test fixture; and/or (vii) rubbing the surface of the object with the piece of rubbing material for a period of time can further comprise rubbing the surface of the object with the piece of rubbing material in a rotational manner or both a rotational manner and a back-and-forth manner in response to an operator command.

The apparatus can comprise: a test fixture that holds an object whose electrostatic charge characteristics are to be measured, and the test fixture further including means for moving a piece of rubbing material into contact with the object and means for rubbing a surface of the object with the piece of rubbing material for a period of time, wherein the rubbing causes an electrostatic charge to be built up on the surface of the object. Optionally, the apparatus can further comprise: (i) the means for measuring the electrostatic charge characteristics of the object; and/or (ii) means for displaying the measured electrostatic charge characteristics of the object; wherein, optionally (i) the means for rubbing the surface of the object with the piece of rubbing material for a period of time can be configured to rub the surface of the object with the piece of rubbing material in a rotational manner and/or in both a rotational manner and in a back-and-forth manner, and, optionally, in response to an operator command; (ii) the means for moving a piece of rubbing material can be configured to move the piece of rubbing material into contact with the object in response to an operator command; (iii) the means for measuring the electrostatic charge characteristics of the object can comprise a tribocharge meter that is configured to measure a peak voltage associated with the measured electrostatic charge and a rate of decay of the voltage associated with the measure electrostatic charge, and, optionally, a voltage recorder that can be configured to numerically display the measured peak voltage and the measured rate of decay of the voltage; (iv) the means for displaying the measured electrostatic charge characteristics of the object can comprise a computer that can be configured to graphically display the measured peak voltage and the measured rate of decay of the voltage.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims. All citations referred herein are expressly incorporated herein by reference.

The invention claimed is:

1. A method for measuring the electrostatic charge characteristics of an object, the method comprising:
    placing the object in a test fixture;
    moving a piece of rubbing material within the test fixture into contact with the object;
    maintaining contact between the piece of rubbing material and a surface of the object while rotationally rubbing the surface of the object with the piece of rubbing material for a period of time, wherein the rubbing causes an electrostatic charge to be built up on the surface of the object;
    measuring the electrostatic charge characteristics of the object; and
    displaying the measured electrostatic charge characteristics of the object.

2. The method of claim 1, wherein moving a piece of rubbing material further comprises automated moving the piece of rubbing material within the text fixture into contact with the object in response to an operator command.

3. The method of claim 1, wherein rubbing a surface of the object with the piece of rubbing material for a period of time further comprises rubbing the surface of the object with the piece of rubbing material in both a rotational manner and in a back-and-forth manner.

4. The method of claim 1, wherein measuring the electrostatic charge characteristics of the object further comprises measuring a peak voltage associated with the measured electrostatic charge and a rate of decay of the voltage associated with the measure electrostatic charge.

5. The method of claim 4, further comprising numerically displaying the measured peak voltage and the measured rate of decay of the voltage.

6. The method of claim 1, wherein displaying the measured electrostatic charge characteristics of the object further comprises graphically displaying the peak voltage associated with the measured electrostatic charge and a rate of decay of the voltage associated with the measure electrostatic charge.

7. The method of claim 1, wherein rubbing a surface of the object with the piece of rubbing material for a period of time further comprises rubbing the surface of the object with the piece of rubbing material in both a rotational manner and a back-and-forth manner in response to an operator command.

8. Apparatus, comprising:
- a test fixture that holds an object whose electrostatic charge characteristics are to be measured;
- the test fixture further including means for moving a piece of rubbing material into contact with the object and means for rotationally rubbing a surface of the object with the piece of rubbing material for a period of time, wherein the rubbing causes an electrostatic charge to be built up on the surface of the object;
- means for measuring the electrostatic charge characteristics of the object.

9. The apparatus of claim 8, further comprising means for displaying the measured electrostatic charge characteristics of the object.

10. The apparatus of claim 8, wherein the means for rubbing a surface of the object with the piece of rubbing material for a period of time is configured to rub the surface of the object with the piece of rubbing material in both a rotational manner and in a back-and-forth manner.

11. The apparatus of claim 8, wherein the means for moving a piece of rubbing material is configured to move the piece of rubbing material into contact with the object in response to an operator command.

12. The apparatus of claim 8, wherein the means for rubbing a surface of the object with the piece of rubbing material for a period of time is configured to rub the surface of the object with the piece of rubbing material in both a rotational manner and a back-and-forth manner in response to an operator command.

13. The apparatus of claim 8, wherein the means for measuring the electrostatic charge characteristics of the object comprises a tribocharge meter that is configured to measure a peak voltage associated with the measured electrostatic charge and a rate of decay of the voltage associated with the measure electrostatic charge.

14. The apparatus of claim 8, wherein the means for displaying the measured electrostatic charge characteristics of the object comprises a voltage recorder that is configured to numerically display the measured peak voltage and the measured rate of decay of the voltage.

15. The apparatus of claim 8, wherein the means for displaying the measured electrostatic charge characteristics of the object comprises a computer that is configured to graphically display the measured peak voltage and the measured rate of decay of the voltage.

16. The method of claim 3, wherein the object is stationary during the rubbing.

17. The apparatus of claim 8, wherein the object is stationary during the rubbing.

18. A method for measuring the electrostatic charge characteristics of an object, the method comprising:
- placing the object in a test fixture;
- moving a piece of rubbing material within the test fixture into contact with the object;
- maintaining contact between the piece of rubbing material and a surface of the object while rotationally rubbing the surface of the object with the piece of rubbing material for a period of time, wherein the rubbing causes an electrostatic charge to be built up on the surface of the object;
- measuring the electrostatic charge characteristics of the object; and
- displaying the measured electrostatic charge characteristics of the object;
- wherein rubbing a surface of the object with the piece of rubbing material for a period of time further comprises rubbing the surface of the object with the piece of rubbing material in both a rotational manner and in a back-and-forth manner; and
- wherein if the object has a surface resistivity of less than or equal to $10^6$ ohms per square, after rubbing, moving the object to a test probe in a movement time, wherein the movement time is less than or equal to 0.1 seconds.

19. The apparatus of claim 8, further comprising means for moving the object to the means for measuring the electrostatic charge characteristics of the object in a movement time, wherein the movement time is less than or equal to 0.1 seconds.

20. The method of claim 1, wherein the rubbing comprises a rotational motion of the piece of rubbing material while the object is in a stationary position.

\* \* \* \* \*